United States Patent
Liu et al.

(10) Patent No.: US 7,964,716 B2
(45) Date of Patent: Jun. 21, 2011

(54) FLUORESCENT PRIMER SYSTEM FOR DETECTION OF NUCLEIC ACIDS (Q PRIMING)

(75) Inventors: Xiao Kun Liu, Singapore (SG); Yan Hong, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 313 days.

(21) Appl. No.: 12/094,333

(22) PCT Filed: Dec. 5, 2006

(86) PCT No.: PCT/SG2006/000378
§ 371 (c)(1),
(2), (4) Date: Oct. 7, 2008

(87) PCT Pub. No.: WO2007/067151
PCT Pub. Date: Jun. 14, 2007

(65) Prior Publication Data
US 2009/0220961 A1 Sep. 3, 2009

Related U.S. Application Data

(60) Provisional application No. 60/741,882, filed on Dec. 5, 2005.

(51) Int. Cl.
*C07H 21/04* (2006.01)
*C07H 19/04* (2006.01)
*C12Q 1/68* (2006.01)
*C12P 19/34* (2006.01)

(52) U.S. Cl. .............. 536/24.3; 536/23.1; 536/24.33; 536/26.6; 435/6; 435/91.1; 435/91.2; 422/61

(58) Field of Classification Search ............. 435/6, 91.1, 435/91.2; 536/23.1, 24.3, 24.33, 26.6; 422/61
See application file for complete search history.

(56) References Cited

FOREIGN PATENT DOCUMENTS
WO 98002449 A1 1/1998

OTHER PUBLICATIONS

Kurata, S., et al. (2001), "Fluorescent Quenching-Based Quantitative Detection of Specific DNA/RNA Using a BODIPU®FL-Labeled Probe or Primer," Nucleic Acids Research, 29(6):e34, pp. 1-5.
Zoe Jordens, J., et al. (2000), "Amplification with Molecular Beacon Primers and Reverse Line Blotting for the Detection and Typing of Human Papillomaviruses," Journal of Virological Methods, 89:29-37.
Nuovo, G.J., et al. (1999), "In Situ Amplification Using Universal Energy Transfer-Labeled Primers," the Journal of Histochemistry & Cytochemistry, 47(3):273-279.
Nazarenko, I.A., et al. (1997), "A Closed Tube Format for Amplification and Detection of DNA Based on Energy Transfer," Nucleic Acids Research, 25(12):2516-2521.
Nazarenko, I., et al. (2002), "Multiplex Quantitative PCR Using Self-Quenched Primers Labeled With a Single Fluorophore," Nucleic Acids Research 30(9):e37, pp. 1-7.

(Continued)

*Primary Examiner* — Jezia Riley
(74) *Attorney, Agent, or Firm* — Rothwell, Figg, Ernst & Manbeck pc

(57) ABSTRACT

The present invention is directed to a self-quenching primer comprising; a fluorophore that can be quenched by guanine; an oligonucleotide sequence that forms a hairpin; an oligonucleotide that is a target specific sequence and; use in amplification reactions, particularly in polymerase chain reactions, during which the fluorophore is released thereby emitting fluorescence.

34 Claims, 7 Drawing Sheets

OTHER PUBLICATIONS

Fiandaca, M.J., et al. (2001), "Self-Reporting PNA/DNA Primers for PCR Analysis," Genome Research, 11:609-613.

Tyagi, S. et al. (1998), "Multicolor Molecular Beacons for Allele Discrimination," Nature Biotechnology, 16:49-53.

Liu, X.K. & Hong, Y. (2007), "Q-Priming PCR: A Quantitative Real-time PCR System Using a Self-Quenched BODIPY FL-Labeled Primer," Analytical Biochemistry, 360:154-156.

Heinlein, T. et al., "Photoinduced Electron Transfer Between Fluorescent Dyes and Guanosine Residues in DNA-Hairpins," Journal of Physical Chemistry B 20030807 American Chemical Society US, Aug. 2003, vol. 107, No. 31, pp. 7957-7964.

Knemeyer, J.P. et al., "Probes for Detection of Specific DNA Sequences at the Single-Molecule Level," Analytical Chemistry, Aug. 2000, vol. 72, No. 16, pp. 3717-3724.

Tani, H. et al., "Quantification of Genetically Modified Soybean by Quenching Probe Polymerase Chain Reaction," Journal of Agricultural and Food Chemistry, American Chemical Society, Washington, US, Apr. 2005, vol. 53, No. 7, pp. 2535-2540.

Communication dated Apr. 17, 2009, Supplementary European Search Report, Applicant: Temasek Life Sciences Laboratory Limited, Application No. 06824649.5-2402 / 1960542 PCT/SG2006000378, 7 pages.

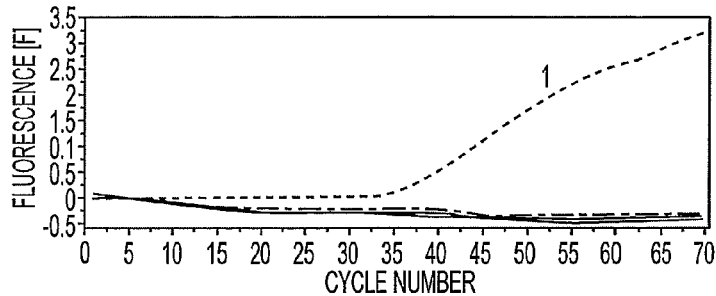

FIG. 10A

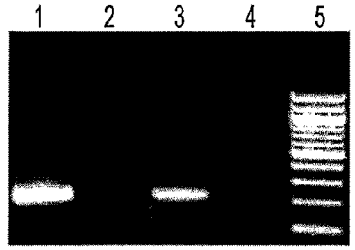

FIG. 10B

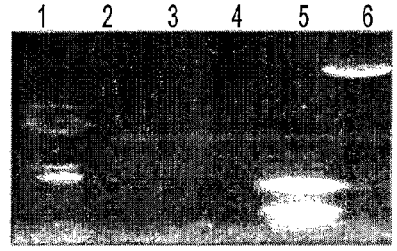

FIG. 10C

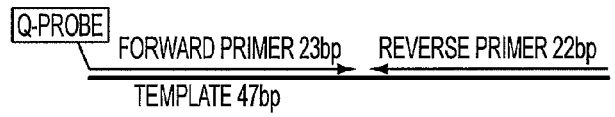

FIG. 11A

| ID | Ct VALUE | | ID | Ct VALUE |
|---|---|---|---|---|
| 10: NORM 3'CC TTGAT ACCCT TTGCG GCGAG5' | 6.9 | | 20: NORM 3'TT CCGAT CCACT TGGCG TCGGA5' | 7.9 |
| 15: CC>AT 3'CC TTGAT AATCT TTGCG GCGAG5' | 9.4 | | 25: TT>GC 3'TT CCGAT CCACGCGGCG TCGGA5' | 11.9 |
| 14: CC>TA 3'TA TTGAT ACCCT TTGCG GCGAG5' | 40.5 | | 24: TT>CG 3'CG CCGAT CCACT TGGCG TCGGA5' | 42.5 |
| 13: C>T 3'CC TTGAT ACTCT TTGCG GCGAG5' | 9.7 | | 23: T>G 3'TT CCGAT CCACG TGGCG TCGGA5' | 10.6 |
| 12: C>A 3'CA TTGAT ACCCT TTGCG GCGAG5' | 9.0 | | 22: T>C 3'TC CCGAT CCACT TGGCG TCGGA5' | 11.7 |
| 11: C>T 3'TC TTGAT ACCCT TTGCG GCGAG5' | 17.8 | | 21: T>C 3'CT CCGAT CCACT TGGCG TCGGA5' | 19.2 |

TEMPLATE1: 5'... GG AACTA TGGGA AACGC CGCTC3'   TEMPLATE2: 5'... AA GGCTA GGTGA ACCGC AGCCT3'

FIG. 11B

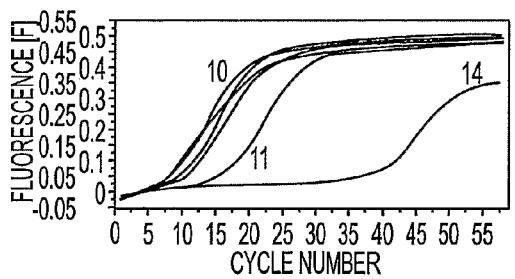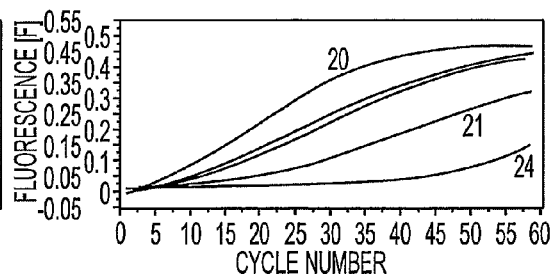

FIG. 11C

```
                         SEQUENCE LISTING

<160> NUMBER OF SEQ ID NOS: 27

<210> SEQ ID NO 1
<211> LENGTH: 20
<212> TYPE: DNA
<213> ORGANISM: Artificial
<220> FEATURE:
<223> OTHER INFORMATION: oligonucletide primer

<400> SEQUENCE: 1
tggggaatct tggacaatgg                                               20

<210> SEQ ID NO 2
<211> LENGTH: 18
<212> TYPE: DNA
<213> ORGANISM: Artificial
<220> FEATURE:
<223> OTHER INFORMATION: oligonucleotide primer

<400> SEQUENCE: 2
ccgattcacc gcctacgt                                                 18

<210> SEQ ID NO 3
<211> LENGTH: 70
<212> TYPE: DNA
<213> ORGANISM: Artificial
<220> FEATURE:
<223> OTHER INFORMATION: oligonucleotide primer

<400> SEQUENCE: 3
cctcgtcgcc gcctgttcct aatacaatag gaacaggcgg cgacgaggga tggggaatct   60
```

```
tggacaatgg                                                              70

<210> SEQ ID NO 4
<211> LENGTH: 70
<212> TYPE: DNA
<213> ORGANISM: Artificial
<220> FEATURE:
<223> OTHER INFORMATION: Oligonucleotide primer

<400> SEQUENCE: 4
cctcgtcgcc gcctgttcct aatacaatag gaacaggcgg cgacgaggga tggggaatct       60
tggacaatgg                                                              70

<210> SEQ ID NO 5
<211> LENGTH: 18
<212> TYPE: DNA
<213> ORGANISM: Artificial
<220> FEATURE:
<223> OTHER INFORMATION: Oligonucleotide primer

<400> SEQUENCE: 5
ccgattcacc gcctacgt                                                     18

<210> SEQ ID NO 6
<211> LENGTH: 50
<212> TYPE: DNA
<213> ORGANISM: Artificial
<220> FEATURE:
<223> OTHER INFORMATION: Oligonucleotide primer

<400> SEQUENCE: 6
cctcgtcgcc atacaaggcg acgaggggag cgtgtctggg gtcctgattc                  50

<210> SEQ ID NO 7
<211> LENGTH: 24
<212> TYPE: DNA
<213> ORGANISM: Artificial
<220> FEATURE:
<223> OTHER INFORMATION: Oligonucleotide primer

<400> SEQUENCE: 7
cggatagggt aggttctgga gtca                                              24

<210> SEQ ID NO 8
<211> LENGTH: 47
<212> TYPE: DNA
<213> ORGANISM: Artificial
<220> FEATURE:
<223> OTHER INFORMATION: Oligonucleotide primer

<400> SEQUENCE: 8
cctcgtcgcc atacaaggcg acgagggtag catctacata tagcttc                     47

<210> SEQ ID NO 9
<211> LENGTH: 19
<212> TYPE: DNA
<213> ORGANISM: Artificial
<220> FEATURE:
<223> OTHER INFORMATION: Oligonucleotide primer

<400> SEQUENCE: 9
gaccaggcca ttcgcctca                                                    19

<210> SEQ ID NO 10
<211> LENGTH: 50
```

```
<212> TYPE: DNA
<213> ORGANISM: Artificial
<220> FEATURE:
<223> OTHER INFORMATION: Oligonucleotide primer

<400> SEQUENCE: 10
cctcgtcgcc atacaaggcg acgaggggag cgtgtctggg gtcctgattc            50

<210> SEQ ID NO 11
<211> LENGTH: 22
<212> TYPE: DNA
<213> ORGANISM: Artificial
<220> FEATURE:
<223> OTHER INFORMATION: Oligonucleotide primer

<400> SEQUENCE: 11
gagcggcgtt tcccatagtt cc                                          22

<210> SEQ ID NO 12
<211> LENGTH: 48
<212> TYPE: DNA
<213> ORGANISM: Artificial
<220> FEATURE:
<223> OTHER INFORMATION: Synthetic target nucleic acid

<400> SEQUENCE: 12
tgagcgtgtc tggggtcctg attcaggaac tatgggaaac gccgctct              48

<210> SEQ ID NO 13
<211> LENGTH: 87
<212> TYPE: DNA
<213> ORGANISM: Artificial
<220> FEATURE:
<223> OTHER INFORMATION: Synthetic target nucleic acid

<400> SEQUENCE: 13
atagcatcta catatagctt ctcgttgtta gaaaaacaaa actatttggg atcggagaag  60
aactgtttga ggcgaatggc ctggtcg                                     87

<210> SEQ ID NO 14
<211> LENGTH: 48
<212> TYPE: DNA
<213> ORGANISM: Artificial
<220> FEATURE:
<223> OTHER INFORMATION: Synthetic target nucleic acid

<400> SEQUENCE: 14
tgagcgtgtc tggggtcctg attcaggaac tatgggaaac gccgctct              48

<210> SEQ ID NO 15
<211> LENGTH: 48
<212> TYPE: DNA
<213> ORGANISM: Artificial
<220> FEATURE:
<223> OTHER INFORMATION: Synthetic target nucleic acid

<400> SEQUENCE: 15
tgagcgtgtc tggggtcctg attcaaaggc taggtgaacc gcagcctt              48

<210> SEQ ID NO 16
<211> LENGTH: 22
<212> TYPE: DNA
<213> ORGANISM: Artificial
<220> FEATURE:
<223> OTHER INFORMATION: Oligonucleotide primer

<400> SEQUENCE: 16
```

```
gagcggcgtt tcccatagtt cc                                          22
```

<210> SEQ ID NO 17
<211> LENGTH: 22
<212> TYPE: DNA
<213> ORGANISM: Artificial
<220> FEATURE:
<223> OTHER INFORMATION: Oligonucleotide primer

<400> SEQUENCE: 17

```
gagcggcgtt tctaatagtt cc                                          22
```

<210> SEQ ID NO 18
<211> LENGTH: 22
<212> TYPE: DNA
<213> ORGANISM: Artificial
<220> FEATURE:
<223> OTHER INFORMATION: Oligonucleotide primer

<400> SEQUENCE: 18

```
gagcggcgtt tcccatagtt at                                          22
```

<210> SEQ ID NO 19
<211> LENGTH: 22
<212> TYPE: DNA
<213> ORGANISM: Artificial
<220> FEATURE:
<223> OTHER INFORMATION: Oligonucleotide primer

<400> SEQUENCE: 19

```
gagcggcgtt tctcatagtt cc                                          22
```

<210> SEQ ID NO 20
<211> LENGTH: 22
<212> TYPE: DNA
<213> ORGANISM: Artificial
<220> FEATURE:
<223> OTHER INFORMATION: Oligonucleotide primer

<400> SEQUENCE: 20

```
gagcggcgtt tcccatagtt ac                                          22
```

<210> SEQ ID NO 21
<211> LENGTH: 22
<212> TYPE: DNA
<213> ORGANISM: Artificial
<220> FEATURE:
<223> OTHER INFORMATION: Oligonucleotide primer

<400> SEQUENCE: 21

```
gagcggcgtt tcccatagtt ct                                          22
```

<210> SEQ ID NO 22
<211> LENGTH: 22
<212> TYPE: DNA
<213> ORGANISM: Artificial
<220> FEATURE:
<223> OTHER INFORMATION: Oligonucleotide primer

<400> SEQUENCE: 22

```
aggctgcggt tcacctagcc tt                                          22
```

<210> SEQ ID NO 23
<211> LENGTH: 22
<212> TYPE: DNA
<213> ORGANISM: Artificial

```
<220> FEATURE:
<223> OTHER INFORMATION: Oligonucleotide primer

<400> SEQUENCE: 23
aggctgcggc gcacctagcc tt                                              22

<210> SEQ ID NO 24
<211> LENGTH: 22
<212> TYPE: DNA
<213> ORGANISM: Artificial
<220> FEATURE:
<223> OTHER INFORMATION: Oligonucleotide primer

<400> SEQUENCE: 24
aggctgcggt tcacctagcc gc                                              22

<210> SEQ ID NO 25
<211> LENGTH: 22
<212> TYPE: DNA
<213> ORGANISM: Artificial
<220> FEATURE:
<223> OTHER INFORMATION: Oligonucleotide primer

<400> SEQUENCE: 25
aggctgcggt gcacctagcc tt                                              22

<210> SEQ ID NO 26
<211> LENGTH: 22
<212> TYPE: DNA
<213> ORGANISM: Artificial
<220> FEATURE:
<223> OTHER INFORMATION: Oligonucleotide primer

<400> SEQUENCE: 26
aggctgcggt tcacctagcc ct                                              22

<210> SEQ ID NO 27
<211> LENGTH: 22
<212> TYPE: DNA
<213> ORGANISM: Artificial
<220> FEATURE:
<223> OTHER INFORMATION: Oligonucleotide primer

<400> SEQUENCE: 27
aggctgcggt tcacctagcc tc                                              22
```

FLUORESCENT PRIMER SYSTEM FOR DETECTION OF NUCLEIC ACIDS (Q PRIMING)

BACKGROUND OF THE INVENTION

The present invention is directed to a self-quenching primer and its use in amplification reactions, particularly in polymerase chain reactions, during which the fluorophore is released thereby emitting fluorescence.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

PCR products can be quantitated during the linear portion of amplification allowing an accurate quantitation of templates. There have been many quantitation methods developed based on PCR amplification. Several of these are summarized below.

Real-time PCR has been the most widely used in which PCR products are monitored in real time mainly through fluorescence emitted in association with PCR products. The several approaches to generate fluorescence in association with PCR products include the use of nucleic acid dyes (e.g. SYBR Green I) and Fluorescence Resonance Energy Transfer (FRET).

Dye-based methods are comparatively simple because specific binding of certain dyes, such as SYBR green I, to double strand DNA will emit fluorescence (FIG. 1). Such methods, however, are not as specific. Since the fluorescence depends solely on the amount of ds DNA, which includes specific products, non-specific products and primer dimers, it is not specific to a particular PCR product.

Fluorescence Resonance Energy Transfer (FRET) (Clegg, 1992) refers to a process by which energy is transferred from one dye molecule (the donor) to another (the acceptor) without the emission of a photon. FRET technology has been used in several ways to develop real time hybridization assays including the Roche FRET assay, TaqMan® assay, molecular beacon and their derivatives. In FRET, if the acceptor dye is a fluorophore, the energy may be emitted as fluorescence that is characteristic of the acceptor dye, otherwise the energy is dissipated and the fluorescence quenched. The Roche FRET assay (FIG. 2) uses two oligonucleotides probes with one carrying the donor and the other one carrying the receptor molecule at their adjacent ends. The binding to the PCR products by the two oligonucleotides puts the two fluorescent dyes close to each other; thereby the acceptor dye will emit fluorescence upon accepting energy from the donor. Fluorescent detection is conducted during the annealing step. This technique is very specific since emission of fluorescence from receptor depends not only on the PCR products but also on specific binding to the PCR products by the two primers. However, it is sometimes difficult to design four primers for one target sequence, especially with two primers adjacent to each other. It is not suitable for short target sequences such as transgenic elements in highly degraded DNA samples. The cost is also a concern since two primers each labeled with one fluorescent dye are required for each target sequence.

Another technique, the TaqMan® assay (Livak et al., 1995), also uses FRET to monitor PCR reactions in real time. It needs two primers and one probe for a target sequence (FIG. 3). The probe is an oligonucleotide complementary to a region between the forward and reverse primer with the fluorescent donor and quenching receptor dye attached to its 5' and 3' ends. The energy transfer from the fluorescent donor to receptor dye will quench fluorescence. This probe will bind to PCR fragment but will later be deleted by DNA polymerase with 5' exonuclease activity. Degradation of the probe will separate the donor from the receptor molecule and hence the donor molecule will emit fluorescence. The TaqMan® assay is as specific as the Roche FRET assay, but requires that the three oligonucleotides be close to each other, an optimal distance between the forward primer and the probe of less than 10 bp while the distance of the probe from the reverse primer as short as possible. Tm for the probe should also be higher than those of forward and reserve primers, preferably by 8° to 10° C. In this method, there is still the need to use two fluorescent dyes for each target sequence.

A derivative of the TaqMan® assay, UT-PCR (Zhang et al., 2003), uses a universal oligonucleotide with two dyes attached at two ends with fluorescent donor quenched by the non-fluorescent quencher. The forward primer has the complementary sequence (universal template) to this oligonucleotide attached to its 5' end. The oligonucleotide will bind to 5' universal sequence of forward primer during annealing. At the end of DNA polymerization in the reverse direction, the oligonucleotide with two dyes will be deleted, releasing the fluorescent donor. This design uses only two specific primers, compatible with general PCR. The main advantage is the potential cost saving by using dyes attached to a universal oligonucleotide. However, it may have the problem of non-linear increase of fluorescence due to competition between the universal oligonucleotide and PCR product for forward primer.

A molecular beacon (FIG. 4) is made up of an oligonucleotide with a fluorescent dye attached to one end and a quencher (non-fluorescent acceptor dye) attached to the other. The sequence is designed so that the oligonucleotide forms a hairpin loop, which brings the fluorescent dye and quencher together. In this configuration, the fluorescence is nearly completely quenched in solution. The loop portion of the hairpin is complementary to the sequence of interest and between the forward and reverse primer. Once hybridization to the sequence on template or PCR products, the hairpin unfolds, separating the fluorescent dye from the quencher. Thus, a fluorescent signal indicates hybridization of the molecular beacon to the sequence of interest and its intensity correlate to the quantity of PCR products. This technique has lower background than others but still requires a tailor made third primer with two dyes. It also has some requirement for the loop portion of the hairpin.

BODIPY® FL developed by Molecular Probes is 4,4-difluoro-5,7-dimethyl-4-bora-3a,4a-diaza-s-indacene-3-propionic acid. Its structure is shown in FIG. 5. It has several characteristics that make it potentially possibility in many applications. These include: high extinction coefficient; high fluorescence quantum yield; spectra that are relatively insensitive to solvent polarity and pH; narrow emission bandwidth which resulting in a higher peak intensity than that of fluorescein; relatively long excited-state lifetimes, making the dyes useful for fluorescence polarization-based assays; little or no spectral overlap with longer-wavelength dyes which making it one of the preferred green-fluorescent dyes for multicolor application; and lack of ionic charge.

BODIPY® FL can be attached to an oligo at 5' by a linker. Horn et al. (1997) reported that the fluorescent emission from a probe modified with fluorophore BODIPY® FL was diminished after hybridization. Kurata et al. (2001) found that the quenching was caused by the interaction between the fluorophore and a guanine base. Furthermore, it is reported that fluorescence intensity decreases much more when guanine is opposite to the fluorophore than at another position. Kurata et al. (2001) used this discovery to design an oligonucleotide probe for the quantitative detection of target DNA. Kurata et al. (2001) also modified a primer by adding a cytosine and BODIPY® FL and used this primer for real-time quantitative PCR. It was found that a guanine was added to the primer during PCR resulting in the quenching of fluorescence. The initial quantity of target present in the sample was determined by utilizing a fluorescence quench rate.

Also making use of this discovery, Tani et al. (2005) designed an oligonucleotide with BODIPY® FL attached to its 3' end that is complementary to a sequence between the forward and the reverse primer. Binding to this oligonucleotide will put the BODIPY® FL just opposite guanines on template DNA and hence its fluorescence quenched. It was found that the decrease of fluorescence when detected after annealing was proportional to the PCR products. This approach, however, is even more stringent on primer design than the Taqman® assay due to the requirement for the presence of at least one guanine on the target sequence for efficient quenching. On the other hand, decrease of fluorescence is not as sensitive and specific due to the presence of heavy fluorescence background in solution.

Thus, there is a long-standing need for the development of primers and systems for use in amplification reactions to improve aspects of primer design and label detection, especially for use in real-time amplification reactions.

SUMMARY OF THE INVENTION

The present invention is directed to a self-quenching primer and its use in amplification reactions, particularly in polymerase chain reactions, during which the fluorophore is released thereby emitting fluorescence.

Thus, in one aspect, the present invention provides a self-quenching primer that comprises the structure: Q-5'-$C_n$—X-$G_{(n+1)}$-$Y_m$—Z-3', wherein n is 0-10, m is 0 or 1, Q is a fluorophore that can be quenched by guanine, X is an oligonucleotide sequence that forms a hairpin, Y is a nucleotide linker sequence and Z is an oligonucleotide that is a target specific sequence. Preferably, n is 0-10, more preferably 0-5, still more preferably 0-1. Y comprises 1-5 nucleotides, preferably 1-2 nucleotides, and more preferably 1 nucleotide. Preferably, the hairpin forming sequence X has a Tm that is no lower than the higher value of Tm for the target specific sequence Z and the PCR extension temperature. Preferably the Tm is 60°-100° C., more preferably, 70°-90° C. and most preferably 80°-85° C. Q may be BODIPY® FL, other variants of BODIPY® dyes as well as other fluorophores, such as fluoresceins, 5-FAM (5-carboxyfluorescein), TAMRA (tetramethyl-6-carboxyrhodamine), and the like. Other dyes which can be quenched by guanine are well known to the skilled artisan. For convenience, the invention will be described herein with reference to Q being BODIPY® FL, but it is understood that other fluorophores that are quenched by guanine can be used in its place.

In a second aspect, the present invention provides methods in which the self-quenching primer is used in conjunction with a linear primer for nucleic acid amplification (e.g., PCR amplification). The methods can be applied to various forms of PCR, including, but not limited to, real-time quantitative PCR, reverse transcription PCR, in situ PCR, multiplex PCR, allele specific PCR, and/or multiplex allele specific PCR, and can be used for single nucleotide discrimination (e.g., SNP detection, allele discrimination, and the like) in real time detection. In the amplification reaction, the self-quenching primer anneals to a target sequence while its 5' sequence forms a hairpin structure with the BODIPY® FL positioned just opposite to the multiple guanines which quench its fluorescence. During the extension step in the opposite direction in the second round and all subsequent rounds of the PCR reaction, a polymerase with inherent 5'-3' exonuclease activity cleaves the hairpin structure of the self-quenching primer releasing the BODIPY® FL. The release of the BODIPY® FL results in fluorescence emission without quenching. The released fluorescence is positively correlated to the PCR products in the system. This system allows real time monitoring of the PCR reaction, and can be used for any purpose that uses PCR to detect the presence of a target nucleic acid. The many applications include, but are not limited to, diagnostics, forensics and testing for genetic modified organisms (GMO). The presence of GMO or transgenic elements of GMO can be detected in raw materials, as part of mixtures (e.g., mixtures of GMO and non-GMO) and in processed products (e.g., food).

In a third aspect, the present invention provides compositions, e.g., for practicing the methods herein or that are produced by the methods herein. For example, the invention provides a composition comprising a template nucleic acid, a self-quenching primer and a linear-primer. The template nucleic acid comprises a first strand, the first strand comprising a target region that comprises a target nucleotide sequence or its reverse complement. The self-quenching primer comprises a region of identity to a 5' subregion of the target region, while the linear primer comprises a region of complementarity to a 3' subregion of the target region. A self-quenching primer can also comprise a region of identity to a 3' subregion of the target region. Alternatively, two self-quenching primers with one comprising a region of identity to a 5' subregion of the target region and the second comprising a region of identity to a 3' subregion of the target region can also be used. The 5' region is located at the 5' end of the target region and the 3' subregion is located at the 3' end of the target region; thus the first and second linear primers define the two ends of the target region.

In a fourth aspect, the present invention provides kits for use in amplifying a target nucleotide sequence or its reverse complement from a template nucleic acid strand that comprises a target region comprising the target nucleotide sequence or its reverse complement. The kit includes a self-quenching primer and a linear primer packaged in one or more containers, and may optionally contain instructions for carrying out the amplification reaction. The self-quenching primer comprises a region of identity to a 5' subregion of the target region, while the linear primer comprises a region of complementarity to a 3' subregion of the target region.

BRIEF DESCRIPTION OF THE FIGURES

FIG. 6A: A detailed design for a Q-primer is shown. In the intact primer, a tight hairpin structure is formed to position BODIPY® FL just opposite a guanidine, which quenches fluorescence from BODIPY® FL. This structure is linked to forward primer sequence (FP) by a linker. FIG. 6B: Binding of the Q-primer to the target sequence does not release the quenching. The forward primer can direct the PCR reaction. FIG. 6C: After the second round of PCR reactions, a reverse primer will bind to the strand with the quenched BODIPY® FL at 5' end. Polymerization will start. FIG. 6D: At the end of polymerization, the exonuclease activity of polymerase will delete the sequence attached to BODIPY® FL, thus releasing the quenching. Fluorescence will be emitted. With the progression of PCR reaction, more fluorescence will be emitted.

FIGS. 10A-10C show that 5'→3' exonuclease releases fluorescence of BODIPY® FL. Q-Priming PCR was used to amplify soybean 18s rDNA. 1, by a DNA polymerase with 5'-3' exonuclease activity (Taq polymerase); 2, negative control with Taq polymerase but no template DNA; 3, by a polymerase without 5'-3' exonuclease activity (Vent exo-); 4, negative control with Vent (exo-) polymerase but no template. FIG. 10A: Fluorescence intensity during progression of PCR reactions. FIG. 10B: Agarose gel electrophoresis of PCR products. 5:100 bp molecular size standards (New England Biolabs). FIG. 10C: Fluorescence detection of PCR products by high performance thin layer chromatography (HPTLC). 5: free BODIPY® FL dye. 6: BODIPY® FL labeled 6 nt as size markers.

FIGS. 11A-11C show mutation discrimination by the Q-priming system. FIG. 11A: Design of mutation detection. FIG. 11B: Details of introduced mutations with corresponding Ct values. The sequence shown for Template 1 comprises nucleotides 26-47 of SEQ ID NO:14. The sequence shown for Template 2 comprises nucleotides 26-47 of SEQ ID NO:15. ID10 to 21 represented PCR reactions with reverse primers mt-rp1 to mt-rp12. The SEQ ID NOs: for these primers are shown in Table 5. Left: C mutated into A or T on reverse primers; Right: T mutated into G or C on reverse primers. FIG. 11C: Amplification plots of real time Q-priming PCR with mutated reverse primers. Identification numbers correlate to IDs for mutations in section B.

FIG. 12A: Fluorescent plot on channel 2 (640 nm), increased fluorescent intensity from TAMRA labeled q-priming PCR(2), no increased fluorescent intensity from BODIPY® FL labeled q-priming PCR(1). FIG. 12B: Fluorescent plot on channel 1 (530 nm). Increased fluorescent intensity from BODIPY® FL labeled q-priming PCR (1), no increased fluorescent intensity from TAMRA labeled q-priming PCR (2).

DETAILED DESCRIPTION OF THE INVENTION

Figure 1:
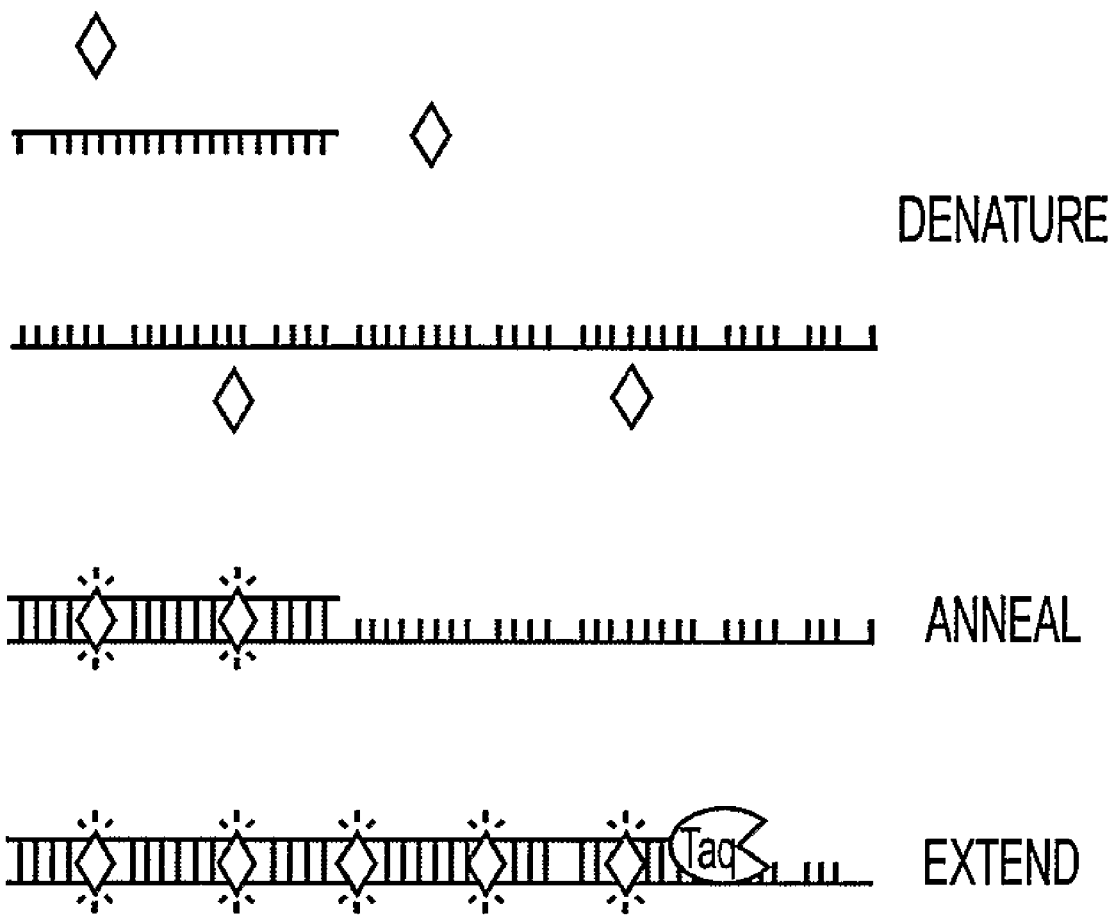
FIG. 1 shows a schematic representation of real-time PCR with the SYBR Green I dye. SYBR Green I dye (black diamonds) becomes fluorescent (gray diamonds) upon binding to double-stranded PCR products.
Figure 2A:
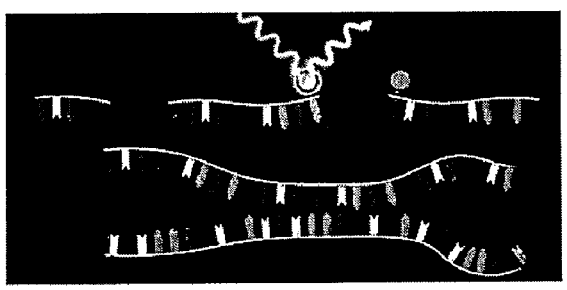
FIGS. 2A-2D show the principles of fluorescence resonance energy transfer (FRET) probes using the LightCycler by Roche. The essential components using fluorescence-labeled oligonucleotides as FRET probes are shown in FIG. 2A: 2 different oligonucleotides (labeled) and the amplification product. Probe 1 bears a fluorescein label at its 3' end, whereas probe 2 has been given another label (LightCycler [LC] Red 640) at its 5' end. The sequences of the 2 probes are selected so that they can hybridize to the amplified DNA fragment in a head-to-tail arrangement, thereby bringing the 2 fluorescent dyes into proximity (FIG. 2B). The first dye (fluorescein) is excited by the light source of the LightCycler and emits green fluorescent light at a slightly longer wavelength. When the 2 dyes are in proximity, the energy thus emitted excites the LC Red 640 attached to the second probe, which subsequently emits red fluorescent light at an even longer wavelength. This energy transfer, referred to as FRET, is highly dependent on the spacing between the 2 dye molecules. Only if the molecules are in proximity (between 1 and 5 nucleotides) is the energy transferred efficiently. The intensity of the light emitted by the LC Red 640 is measured in channel 2 (640 nm) of the LightCycler's optics. The increasing amount of measured fluorescence is proportional to the increasing amount of DNA generated during the ongoing polymerase chain reaction (PCR) process. Since LC Red 640 emits a signal only when both oligonucleotides are hybridized, fluorescence is measured after the annealing step (FIG. 2B). Hybridization does not occur during the denaturation phase of the PCR (FIG. 2A), and fluorescence cannot be detected at 640 nm. After annealing, the temperature is raised, and the hybridization probe is displaced by the Taq DNA polymerase (FIG. 2C). At the end of the elongation step, the PCR product is double stranded, and the probes are too far apart to allow FRET (FIG. 2D).
Figure 2B:
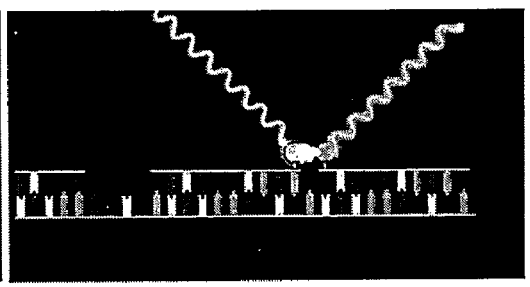
Figure 2C:
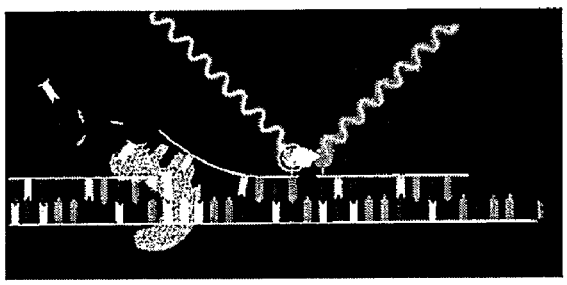
Figure 2D:
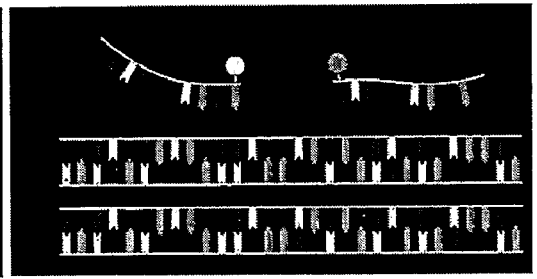
Figure 3:
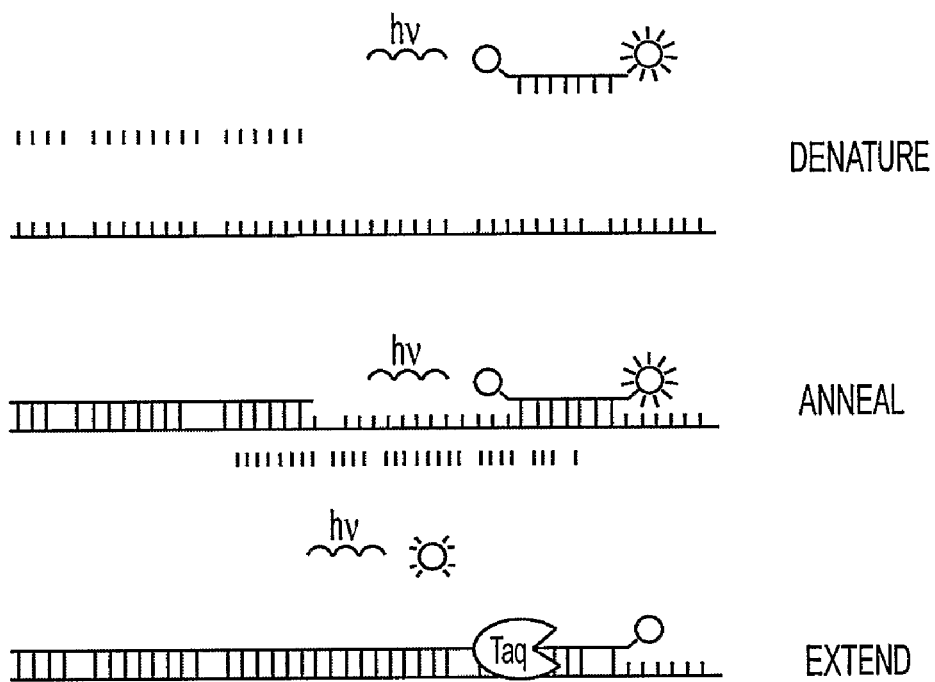
FIG. 3 shows a schematic representation of real-time PCR with TaqMan® primers. In the intact TaqMan® probe, energy is transferred (via FRET) from the short wavelength fluorophore on one end to the long wavelength fluorophore on the other end, quenching the short wavelength fluorescence. After hybridization, the probe is susceptible to degradation by the exonuclease activity of a processing Taq polymerase. Upon degradation, FRET is interrupted, increasing the fluorescence from the short wavelength fluorophore and decreasing the fluorescence from the long wavelength fluorophore.
Figure 4:
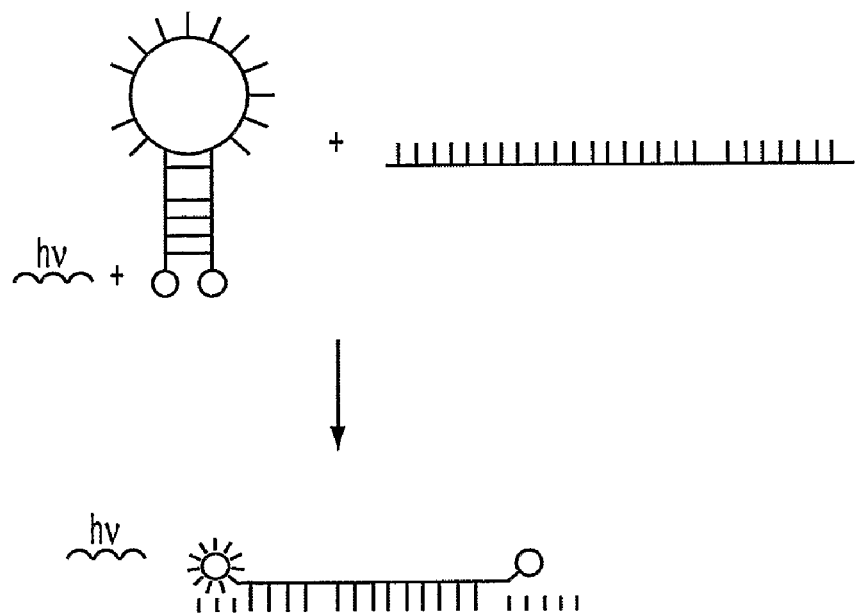
FIG. 4 shows a schematic representation of molecular beacons. In the hairpin loop structure, the quencher (black circle) forms a non-fluorescent complex with the fluorophore (gray circle). Upon hybridization of the molecular beacon to a complementary sequence, the fluorophore and quencher are separated, emitting fluorescence.
Figure 5:
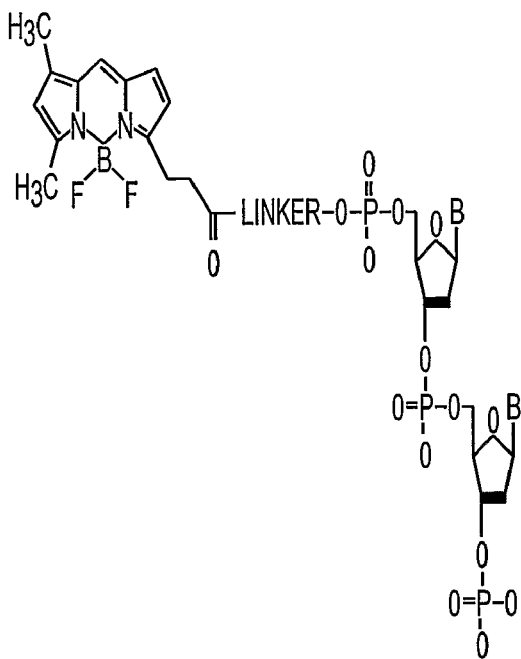
FIG. 5 shows the chemical structure of BODIPY® FL.

The present invention is directed to a self-quenching primer and its use in amplification reactions, particularly in polymerase chain reactions, during which the fluorophore is released thereby emitting fluorescence.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

A "nucleotide sequence" is a polymer of nucleotides (an oligonucleotide, a DNA, a nucleic acid, etc.) or a character string representing a nucleotide polymer, depending on context. Either the given nucleic acid or the complementary nucleic acid can be determined from any specified nucleotide sequence.

An "oligonucleotide" is a polymer comprising two or more nucleotides. The polymer can additionally comprise non-nucleotide elements such as labels, quenchers, blocking groups, or the like. The nucleotides of the oligonucleotide can be natural or non-natural and can be unsubstituted, unmodified, substituted or modified. The nucleotides can be linked by phosphodiester bonds, or by phosphorothioate linkages, methylphosphonate linkages, boranophosphate linkages, or the like.

A "primer" is a nucleic acid that contains a sequence complementary to a region of a template nucleic acid strand and that primes the synthesis of a strand complementary to the template (or a portion thereof). Primers are typically, but need not be, relatively short, chemically synthesized oligonucleotides (typically, deoxyribonucleotides). In an amplification reaction, e.g., PCR amplification, a pair of primers typically define the 5' ends of the two complementary strands of the nucleic acid target that is amplified. In order to be extendable by a standard polymerase, a primer typically has a free 3' hydroxyl group.

A "hairpin primer" is a single nucleic acid molecule that comprises self-complementary sequences and is thus capable of folding back on itself under appropriate conditions. Typically, a hairpin primer comprises a pair of complementary sequences that are able to base pair and form a double-stranded stem, where the complementary sequences are connected by one or more nucleotides, peptide nucleic acid (PNA) monomers, or the like that are able to form a loop or sharp bend (or otherwise allow base pairing to occur between the complementary sequences forming the stem). Like any primer, a hairpin primer typically has a free 3' hydroxyl.

A "linear primer" is a single-stranded nucleic acid molecule that does not comprise self-complementary sequences and thus does not fold back on itself to form a defined secondary structure.

A "target region" or "target sequence" is a region of a nucleic acid that is to be amplified, detected or both.

A "reverse complement" or "complement" or "complementary nucleic acid" is a nucleotide sequence that is fully complementary to given nucleotide sequence. For example, for the given nucleotide sequence 5'-atgcgtt-3', the reverse complement "5'-aacgcat-3' is fully complementary to the given nucleotide sequence.

The "Tm" (melting temperature) of a nucleic acid duplex under specified conditions is the temperature at which half of the base pairs are disassociated and half are associated.

"5' to 3' nuclease activity" is an enzymatic activity that includes either a 5' to 3' exonuclease activity, whereby nucleotides are removed from the 5' end of a nucleic acid strand (e.g., an oligonucleotide) in a sequential manner; or a 5' to 3' endonuclease activity, wherein cleavage occurs more than one nucleotide from the 5' end; or both. An example of 5' to 3' endonuclease activity is the flap endonuclease activity exhibited by the *Thermus aquaticus* DNA polymerase Taq.

In "multiplex PCR" a plurality of target sequences are amplified by a single PCR (i.e., are amplified simultaneously) using a primer pool for amplifying each target sequence.

In "allele specific PCR" selective amplification of a wild type or mutant target sequence is achieved by designing a primer that will match/mismatch one of the alleles at the 3'-end of the primer.

Figure 6:
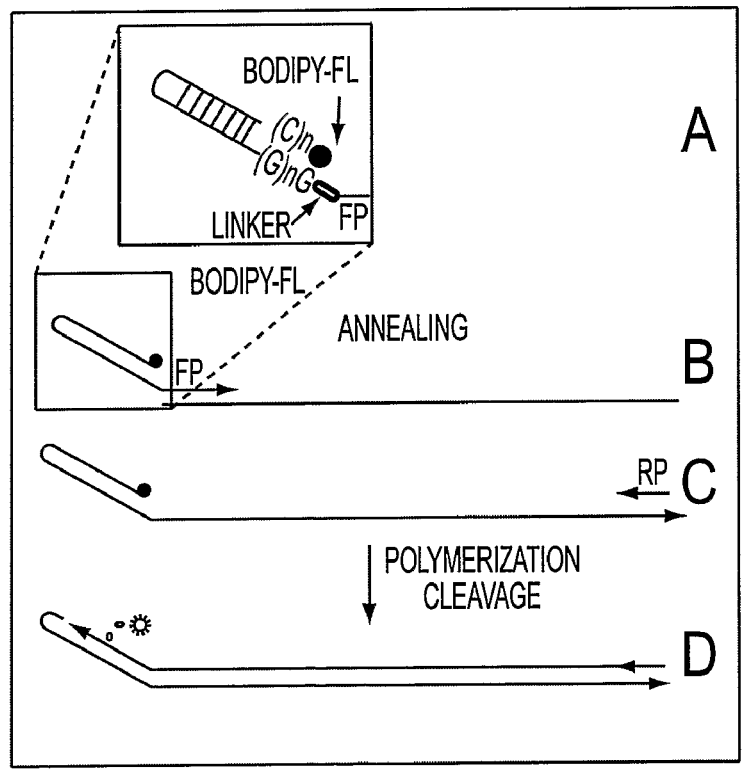
FIGS. 6A-6D shows an illustration of Q-priming system in accordance with the present invention.

In accordance with the present invention, a self-quenching primer is prepared with a BODIPY® FL (as well as other variants of BODIPY® dyes and other fluorophores, such as fluoresceins and TAMRA, that can be quenched by guanine) attached to its 5' end followed by multiple cytosines (n), a sequence for forming hairpin structure, followed by (n+1) guanines that is linked (direct or through a linker sequence) to a specific priming sequence (FIG. 6). The 3' sequence of this self-quenching primer anneals to a target sequence while the 5' sequence forms a hairpin structure with the BODIPY® FL positioned just opposite to multiple guanines. In this manner, fluorescence from BODIPY® FL is quenched. During the extension step in the opposite direction in the second round of PCR reaction, a PCR polymerase with inherent 5'-3' nuclease activity cleaves the hairpin structure of the primer releasing BODIPY® FL. The release of BODIPY® FL results in fluorescence emission without quenching. BODIPY® FL will be released in the same way in all subsequent extension steps.

In one embodiment, the self-quenching primer has the structure: Q-5'-$C_n$—X-$G_{(n+1)}$-$Y_m$—Z-3', wherein n is 0-10, m is 0 or 1, Q is a fluorophore that can be quenched by guanine, X is an oligonucleotide sequence that forms a hairpin, Y is a nucleotide linker sequence and Z is an oligonucleotide that is a target specific sequence. Preferably, n is 0-10, more preferably 0-5, still more preferably 0-1. Y comprises 1-5, nucleotides, preferably 1-2 nucleotides and more preferably 1 nucleotide. Q may be BODIPY® FL, other variants of BODIPY® dyes as well as other fluorophores, such as fluoresceins (including, for example, 5-FAM (5-carboxyfluorescein)), TAMRA (tetramethyl-6-carboxyrhodamine), and the like. The self-quenching primer may be designed as either a forward or a reverse type.

A self-quenching primer comprises hairpin at 5' portion and linear primer at 3' portion. The hairpin possess a "stem and loop" structure, the length and the GC content of the stem sequence is designed in such a way that at the extension temperature of PCR, the hairpin remain closed and fluorescence from BODIPY® FL quenched by G at its opposite position. This is ensured by choosing a stem that melts 8°-10° C. higher than the extension temperature of PCR. In general PCR, extension temperature is 70°-72° C., so we design to melt loop-stem at 80°-90° C. The melting temperature of the stem cannot be predicted by the intermolecular rule used for general PCR primer since the stem is created by intramolecular hybridization. Instead, a DNA folding program, such as Zuker DNA folding program is utilized to estimate the melting temperature of the stem. In general, 9-11 GC-rich stems will melt between 70°-90° C. The loop portion of the hairpin structure X comprises 5-10 nucleotides, preferably 6-8 nucleotides in length. Preferably, the hairpin forming sequence X has a Tm that is higher than the Tm for the target specific sequence Z and PCR extension temperature. Preferably the Tm is 60°-100° C., more preferably, 70°-90° C. and most preferably 80°-85° C.

Z is an oligonucleotide that is a target specific sequence, i.e., Z has identity, preferably complete identity, to a target region of a template nucleic acid. The target specific sequence Z according to the present invention is formed of 5 to 40 bases, preferably 15 to 30 bases, most preferably 20 to 25 bases. A base number greater than 50 leads to lower permeability through a cell membrane when employed in in situ amplification reactions, thereby narrowing an applicable range of the present invention. A base number smaller than 5, on the other hand, tends to induce non-specific hybridization and, therefore, results in a large determination error. No particular limitation is imposed on the base sequence of the target specific sequence Z insofar as the target specific sequence Z hybridizes specifically to the template nucleic acid.

The template nucleic acid can be, e.g., any single-stranded or double-stranded DNA. For example, in one embodiment, the template nucleic acid is a single-stranded DNA product of a reverse transcription reaction (e.g., the self-quenching primer can be conveniently used to detect RNA targets by reverse transcription-PCR, including quantitative reverse transcription-PCR). As other examples, the template nucleic acid can be a synthetic oligonucleotide, a double-stranded cDNA, a single-stranded PCR product, or a double-stranded PCR product or can comprise genomic DNA.

The template nucleic acid can be derived from essentially any source, including, but not limited to: a human; an animal; a plant; a bacterium; a virus; a genetically modified organism, cultured cells or culture medium; a tissue or fluid, e.g., from a patient, such as skin, blood, sputum, urine, stool, semen, or spinal fluid; a tumor; a biopsy; and/or the like.

There are several advantages to the design of the primer in accordance with the present invention. These advantages include:

Cost effectiveness: The invention only utilizes one dye. Synthesis is simpler and more cost-effective than those FRET systems requiring two or more dyes (donor and receptor).

Simple primer design: In Q priming system, the design for 5' portion of one PCR primer can be uniform in the format of BODIPY® FL attached to the 5' end followed by multiple cytosines (n), a sequence for forming hairpin structure, followed by (n+1) guanines. Only the 3' end portion needs to be specific to a target sequence. In comparison, systems with two or more dyes require a proper positioning of probes with respect to one another in order to accomplish the energy transfer, which usually can only be achieved by trial and error, making it a very time-consuming and costly step.

Short fragment PCR is possible: Q priming system uses only two primers complementary to target sequence. This enables the design of short fragment PCR system suitable for detecting degraded DNA from sources such as processed foods, high decomposed biological materials and DNAs from fossils or preserved voucher materials.

Less complexity for multiplexing PCR: Almost all probe-based technologies have inherent complexities related to the kinetics of the hybridization and amplification. In Q priming system, each target needs only two PCR primers with no need of probe, making it less complex for multiplexing PCR.

Lower background: The fluorescence will be perfectly quenched in solution or after primer binding because BODIPY® FL and its quenching sequences are in the same oligonucleotide. Fluorescence will only be emitted after BODIPY® FL is released by exonuclease activity of the polymerase in the PCR reaction. This system gives low background of fluorescence, making detection of specific PCR products potentially more sensitive and specific.

In the amplification methods using the self-quenching primer of the present invention, a template nucleic acid, the self-quenching primer and a linear primer are provided. The template nucleic acid comprises a first strand, the first strand comprising a target region that comprises the target nucleotide sequence or its reverse complement. The self-quenching primer comprises a region of identity, preferably complete identity, to a 5' subregion of the target region, while the linear primer comprises a region of complementarity to a 3' subregion of the target region. The 5' subregion is located at the 5' end of the target region and the 3' subregion is located at the 3' end of the target region; thus, the self-quenching and linear primers define the two ends of the target region. At least a portion of the target nucleotide sequence or its reverse complement is amplified by contacting the template nucleic acid, the self-quenching primer and the linear primer and extending the primers. During the extension step in the opposite direction in the second round of PCR reaction, a PCR polymerase with inherent 5'-3' nuclease activity cleaves the hairpin structure of the primer releasing BODIPY® FL. The release of BODIPY® FL results in fluorescence emission without quenching.

The fluorescent signal emitted by the label is detected. The signal can be detected at any suitable point or points during the amplification; for example, the signal can be detected during each annealing step during PCR cycles. As another example, the signal can be detected after each extension step during PCR, and/or at any other point during the PCR cycles except during the denaturation step. In some embodiments, the intensity of the fluorescent signal is measured (e.g., at each PCR cycle for quantitative real-time PCR).

The present invention also includes compositions, systems, and kits, e.g., for practicing the methods herein or which are produced by the methods herein. In one embodiment, the invention provides a composition comprising a template nucleic acid, a self-quenching linear primer and a linear primer. The template nucleic acid comprises a first strand, the first strand comprising a target region that comprises a target nucleotide sequence or its reverse complement. The self-quenching primer comprises a region of identity, preferably complete identity, to a 5' subregion of the target region, while the linear primer comprises a region of complementarity to a 3' subregion of the target region. The 5' subregion is located at the 5' end of the target region and the 3' subregion is located at the 3' end of the target region; thus the self-quenching and linear primers define the two ends of the target region.

The composition can optionally include a polymerase, preferably a polymerase that has 5' to 3' nuclease activity (e.g., Taq polymerase). The composition can optionally also include other reagents required to amplify a nucleic acid target, for example, deoxyribonucleotides triphosphates, an aqueous buffer, appropriate salts and metal cations, and/or the like.

In one aspect, the invention includes systems and devices for use of the compositions, e.g., according to the methods herein. In one embodiment, the composition is contained in a thermal cycler (e.g., in one or more sample tubes or one or more wells of a multiwell plate, in a reaction region of a thermal cycler, e.g., an automated thermal cycler). The system can include, e.g., a computer with appropriate software for controlling the operation of the thermal cycler (e.g., temperature and duration of each step, ramping between steps, and/or number of cycles) coupled to the thermal cycler. Similarly, the system can include a detector coupled to the thermal cycler and/or computer (e.g., for measuring the fluorescence spectrum and/or intensity from one or more wells of a multiwell plate contained in the reaction region of the thermal cycler after excitation by laser light source).

The computer typically includes appropriate software for receiving user instructions, either in the form of user input into a set of parameter fields, e.g., in a GUI, or in the form of preprogrammed instructions, e.g., preprogrammed for a variety of different specific operations. The software optionally converts these instructions to appropriate language for instructing the operation of the thermal cycler to carry out the desired operation. The computer can also receive data from the thermal cycler and/or detector regarding fluorescent intensity, cycle completion or the like and can interpret the data, provide it to a user in a human readable format, or use that data to initiate further operations (e.g., additional thermal cycles), in accordance with any programming by the user.

Another aspect of the invention provides kits. Thus, one embodiment provides a kit for use in amplifying a target nucleotide sequence or its reverse complement from a template nucleic acid strand that comprises a target region comprising the target nucleotide sequence or its reverse complement. The kit includes a self-quenching primer and a linear primer packaged in one or more containers. The self-quenching primer comprises a region of identity, preferably complete identity, to a 5' subregion of the target region, while the linear primer comprises a region of complementarity to a 3' subregion of the target region. The 5' subregion is located at the 5' end of the target region and the 3' subregion is located at the 3' end of the target region; thus the self-quenching and linear primers define the two ends of the target region.

The kit optionally also includes one or more of: a polymerase (e.g., a polymerase having or 5' to 3' nuclease activity), a buffer, a standard template for calibrating a detection reaction, instructions for extending the hairpin primer to amplify at least a portion of the target nucleotide sequence or reverse complement thereof, instructions for using the components to amplify, detect and/or quantitate the target nucleotide sequence or reverse complement thereof, or packaging materials.

Nucleic acid amplification by template-directed, enzyme-dependent extension of primers is well known in the art. For example, amplification by the polymerase chain reaction (PCR) has been described. Details regarding various PCR methods, including, e.g., asymmetric PCR, reverse transcription-PCR, in situ PCR, quantitative PCR, real time PCR, and multiplex PCR, are well described in the literature. Details regarding PCR methods and applications thereof are found, e.g., in Sambrook et al., *Molecular Cloning—A Laboratory Manual* (3rd Ed.), Vol. 1-3, Cold Spring Harbor Laboratory, Cold Spring Harbor, N.Y. (2000); F. M. Ausubel et al. (eds.), *Current Protocols in Molecular Biology*, Current Protocols, a joint Venture between Greene Publishing Associates, Inc. and John Wiley & Sons, Inc., (supplemented through 2002); Innis et al. (eds.), *PCR Protocols: A Guide to Methods and Applications*, Academic Press Inc., San Diego, Calif. (1990); J. P. V. Heuvel, *PCR Protocols in Molecular Toxicology*, CRC Press (1997); H. G. and A. Griffin, PCR Technology: Current Innovations, CRC Press (1994); Bagasra et al., (1997) *In Situ PCR Techniques*, Jossey-Bass; Bustin (2000); Poddar (2000; and Mackay et al. (2002), among many other references. Additional details regarding PCR methods, including asymmetric PCR methods, multiplexing PCR methods and allele specific PCR methods, are found in the patent literature, e.g., U.S. Pat. No. 5,066,584; U.S. Pat. No. 5,521,301; U.S. Pat. No. 5,582,989; U.S. Pat. No. 5,639,611; U.S. Pat. No. 5,691, 146; U.S. Pat. No. 5,981,176; U.S. Pat. No. 6,391,544; U.S. Pat. No. 7,008,771; and U.S. published patent application No. 2003/0134307 A1 and in the literature, e.g., Edwards and Gibbs (1994); Henegariu et al. (1997); Schmalzing et al. (1999); Rhodes et al. (1997); and Myakishev et al. (2001).

In brief, PCR typically uses at least one pair of primers (typically synthetic oligonucleotides). Each primer hybridizes to a strand of a double-stranded nucleic acid target that is amplified (the original template may be either single-stranded or double-stranded). A pair of primers typically flanks a nucleic acid target that is amplified. Template-dependent extension of the primers is catalyzed by a DNA polymerase, in the presence of deoxyribonucleoside triphosphates (typically dATP, dCTP, dGTP, and dTTP, although these can be replaced and/or supplemented with other dNTPs, e.g., a dNTP comprising a base analog that Watson-Crick base pairs like one of the conventional bases, e.g., uracil, inosine, or 7-deazaguanine), an aqueous buffer, and appropriate salts and metal cations (e.g., $Mg^{2+}$). The PCR process typically involves cycles of three steps: denaturation (e.g., of double-stranded template and/or extension product), annealing (e.g., of one or more primers to template), and extension (e.g., of one or more primers to form double-stranded extension products). The PCR process can instead, e.g., involve cycles of two steps: denaturation (e.g., of double-stranded template and/or extension product) and annealing/extension (e.g., of one or more primers to template and of one or more primers to form double-stranded extension products). The cycles are typically thermal cycles; for example, cycles of denaturation at temperatures greater than about 90° C., annealing at 50-75° C., and extension at 60-78° C. A thermostable enzyme is thus preferred. Automated thermal cyclers, including integrated systems for real time detection of product, are commercially available, e.g., the ABI Prism®. 7700 sequence detection system from Applied Biosystems, the iCycler iQ® real-time PCR detection system from Bio-Rad, or the DNA Engine Opticon® continuous fluorescence detection system from MJ Research, Inc. Thermostable enzymes (including *Thermus aquaticus* Taq DNA polymerase), appropriate buffers, etc. are also widely commercially available, e.g., from Clontech, Invitrogen, Sigma-Aldrich, and New England Biolabs.

A number of variations on the basic PCR technique are known in the art and can be adapted to the practice of this invention. For example, in in situ PCR, PCR amplification is performed in fixed cells, and the amplified target can remain largely within the cell (or organelle etc.) which originally contained the nucleic acid template. Quantitative PCR can be employed, e.g., to determine the amount (relative or absolute) of target initially present in a sample. In real time PCR, product formation is monitored in real time. In real time quantitative PCR with fluorescent detection of product, a fluorescence threshold above background is typically assigned, and the time point at which each reaction's amplification plot reaches that threshold (defined as the threshold cycle number or Ct) is determined. The Ct value can be used to calculate the quantity of template initially present in each reaction. (Under a standard set of conditions, a lower or higher starting template concentration produces a higher or lower, respectively, Ct value.) In multiplex PCR, multiple target sequences can be amplified, detected, and/or quantitated simultaneously in one reaction mixture. Multiple dyes can be used to detect the amplified products in multiplex PCR. In reverse transcription-PCR, reverse transcription of an RNA (e.g., an mRNA) produces a single-stranded DNA template that is used in subsequent PCR cycles. Combinations of such techniques (e.g., quantitative real time reverse transcription-PCR) are routine.

Multiplexing PCR can be performed with two dyes attached to two Q-primers for the amplification of independent target sequences. One dye can be used as internal control or used to detect the second target. For example, TAMRA can be attached to one Q-primer for amplifying a first target sequence and BODIPY® FL can be attached to a second Q-primer for amplifying a second target sequence. In one embodiment, one channel in a multiplex PCR can be used to detect a conserved region while the other channel is used to detect the presence of a variable region. In another embodiment, multiplex PCR can be used for the multiplex detection of hemagglutinin subtypes (H1-H15) by one channel and neuraminidase subtypes (N1-N9) by another channel.

Design of linear primers, e.g., the target specific sequence Z of the present invention, for nucleic acid amplification is routine for one of skill. Design of PCR primers, for example, is described in many of the above references that detail PCR methods.

Design of hairpin primers, including fluorogenic hairpin primers, has also been described, herein and in, e.g., U.S. Pat. No. 6,277,607; U.S. Pat. No. 5,866,336; Kaboev et al. (2000); and Nazarenko et al. (1997).

Design of the hairpin portion of the self-quenching primer of the present invention is preferably performed using software which enables thermodynamic modeling of the hairpin structure, e.g., Mfold DNA server (http://www.bioinfo.rpi.edu/application-s/mfold/old/dna/form1.ci). Preferably, the sequence of the hairpin is designed using such software such that there is only a single predicted stable secondary structure for the hairpin, i.e. only one predicted structure containing a self-complementary double-stranded region that has a negative free energy (ΔG), such that this one structure is the desired hairpin, e.g., with perfectly complementary 5' and 3' arms that form a hairpin structure.

In accordance with the present invention, it is preferred that each of the 5' and 3' arms forming the hairpin structure X of the self-quenching primer comprises 7-15 nucleotides, more preferably 8-11 nucleotides and most preferably 8-10 nucleotides in length. The loop portion of the hairpin structure X comprises 5-10 nucleotides, preferably 6-8 nucleotides in length. Preferably, the hairpin forming sequence X has a Tm that is higher than the Tm for the target specific sequence Z. Preferably the Tm is 60°-100° C., more preferably, 70°-90° C. and most preferably 80°-85° C.

Fluorescent emissions can be detected by essentially any method known in the art. In the context of real time PCR, for example, fluorescent emissions can be conveniently detected during the amplification by use of a commercially available integrated system such as, e.g., Roche Lightcycler® the ABI Prism® 7700 sequence detection system from Applied Biosystems, the iCycler iQ® real-time PCR detection system from Bio-Rad, or the DNA Engine Opticon® continuous fluorescence detection system from MJ Research, Inc.

Self-quenching primers can be synthesized using conventional methods. For example, oligos can be synthesized on commercially available automated oligonucleotide synthesis machines using standard methods. Labels can be attached to the oligos either during automated synthesis or by post-synthetic reactions which have been described before; see, e.g., Tyagi and Kramer (1996), Nelson, et al. (1989), U.S. Pat. No. 6,277,607 and U.S. Pat. No. 5,925,517.

In general, synthetic methods for making oligonucleotides (including labeled oligos) are well known. For example, oligonucleotides can be synthesized chemically according to the solid phase phosphoramidite triester method described by Beaucage and Caruthers (1981), e.g., using a commercially available automated synthesizer, e.g., as described in Needham-VanDevanter et al. (1984). Synthesis of modified oligonucleotides (e.g., oligonucleotides comprising 2'-O-methyl nucleotides and/or phosphorothioate, methylphosphonate, or boranophosphate linkages, e.g., for use as nuclease resistant primers) are described in e.g., *Oligonucleotides and Analogs* (1991), IRL Press, New York; Shaw et al. (1993); Nielsen et al. (1991); and Shaw et al. (2000).

To label the oligonucleotide with the fluorescent dye, one of conventionally-known labeling methods can be used (Tyagi and Kramer (1996); Schofield et al. (1997); Proudnikov and Mirzabekov (1996)). In one embodiment for conjugating a fluorescent dye molecule to the 5' end, a spacer, for example, —$(CH_2)_n$—SH, is first introduced into a phosphate group at the 5' end by a method known in the art. A spacer-introduced derivative is commercially available (Midland Certified Reagent Company). In the above-mentioned example, n ranges from 3 to 8 with 6 being preferred. A labeled oligonucleotide can be synthesized by conjugating an SH-reactive fluorescent pigment or a derivative thereof with the spacer. The thus-synthesized oligonucleotide, which is labeled with the fluorescent dye, can be purified by reversed phase chromatography or the like to provide a nucleic acid probe for use in the present invention.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al, 1989, *Molecular Cloning,* 2nd Ed. (Cold Spring Harbor Laboratory Press, Cold Spring Harbor, N.Y.); Sambrook and Russell, 2001, *Molecular Cloning,* 3rd Ed. (Cold Spring Harbor Laboratory Press, Cold Spring Harbor, N.Y.); Ausubel et al., 1992, *Current Protocols in Molecular Biology* (John Wiley & Sons, including periodic updates); Glover, 1985, *DNA Cloning* (IRL Press, Oxford); Anand, 1992; Guthrie and Fink, 1991; Harlow and Lane, 1988, *Antibodies,* (Cold Spring Harbor Laboratory Press, Cold Spring Harbor, N.Y.); Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology,* 6th Edition, Blackwell Scientific Publications, Oxford, 1988; Hogan et al., *Manipulating the Mouse Embryo,* (Cold Spring Harbor Laboratory Press, Cold Spring Harbor, N.Y., 1986); Westerfield, M., *The zebrafish book. A guide for the laboratory use of zebrafish (Danio rerio),* (4th Ed., Univ. of Oregon Press, Eugene, 2000).

EXAMPLES

The present invention is described by reference to the following Examples, which are offered by way of illustration and is not intended to limit the invention in any manner. Standard techniques well known in the art or the techniques specifically described below were utilized.

Example 1

Detection of 18S rDNA in Soybean Genomic DNA

Firstly, PCR primer pair F3/B3 (Table 1) was used to amplify a 219 bp fragment (FIG. 8) of 18S rDNA (gi343347) in soybean genomic DNA. Primer 1 (Table 1) was designed with BODIPY®-FL attached to CC, followed by 46 nt that form a tight loop stem structure (FIG. 6A).

Figure 7:
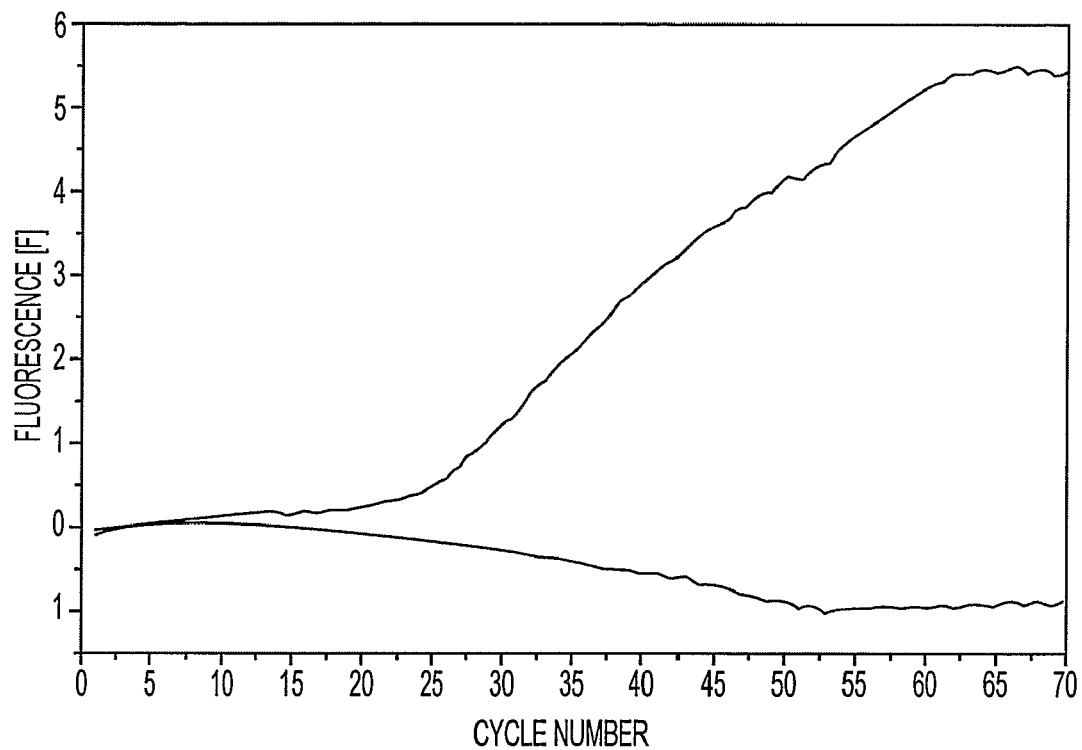
FIG. 7 shows a real-time fluorescence recording for a PCR system to amplify the 219 bp 18S rDNA region using primer 1/B3 primers with soybean genomic DNA as template. The upper line is real-time PCR with soybean genomic DNA and lower line is real-time PCR without template.
Figures 8, 9:
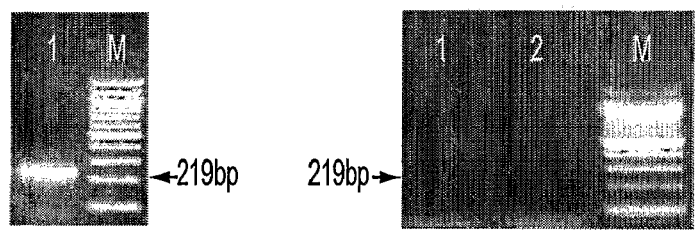
FIG. 8 shows PCR amplification of a 219 bp region in 18S rDNA using F3/B3 primers. Lane 1: Soybean genomic DNA; lane M: 100 bp size markers.
FIG. 9 shows an agarose gel (2.0%) electrophoresis of real-time PCR products as shown in FIG. 7 using primer 1/B3 primers. Lane 1: real-time PCR with soybean genomic DNA; lane 2: real-time PCR without template; lane M: 100 bp molecular markers.
Figure 12A:
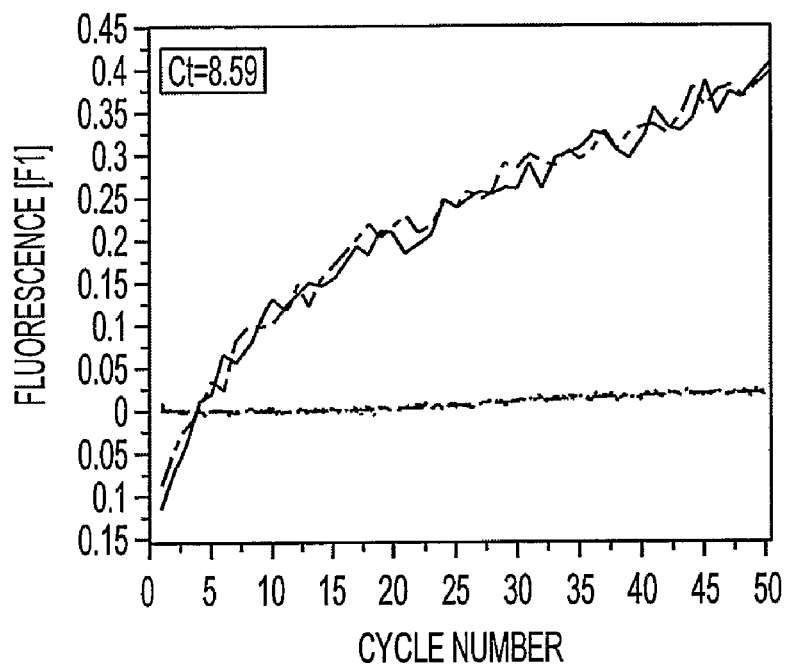
FIGS. 12A and 12B show amplification plots using dual color real time Q-priming PCR system with BODIPY® FL and TAMRA labeled probes in one tube.
Figure 12B:
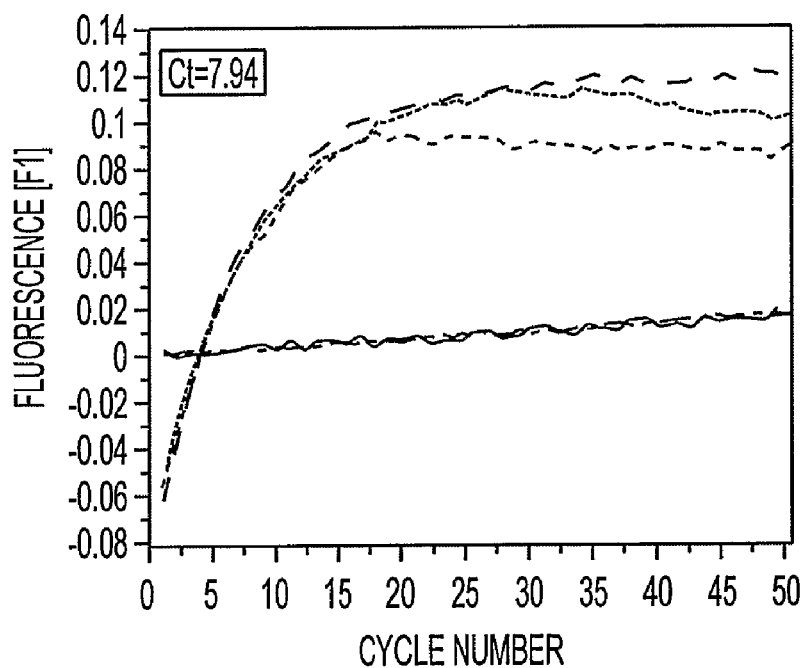

Secondly, primer 1/B3 was used in a real time PCR system with soybean genomic DNA with a Roche Lightcycler real-time PCR machine. Fluorescence (channel 1) was monitored at the end of extension for each PCR cycle until cycle 70 (FIG. 7). To confirm the results, PCR products from this reaction were analyzed on 2.0% agarose gel (FIG. 9).

TABLE 1

Sequences of Primers

| | |
|---|---|
| F3: | 5' tgg gga atc ttg gac aat gg 3' (SEQ ID NO: 1) |
| B3: | 5' ccg att cac cgc cta cgt 3' (SEQ ID NO: 2) |
| Primer 1: | BODIPY ® FL-5' cct cgt cgc cgc ctg ttc cta ata caa tag gaa cag gcg gcg acg agg gat ggg gaa tct tgg aca atg g 3' (SEQ ID NO: 3) |

F3/B3 amplified a discrete DNA fragment of size between 219 bp in reference of DNA size standard (100 bp ladder, Biolabs, MA) as shown in FIG. 8.

Secondly, primer 1/B3 was used in a real time PCR system with soybean genomic DNA as the template (FIG. 7). In the sample tube (blue line), emission of fluorescence was monitored from 25 cycles onwards. Its intensity increased for every cycle until reaching a plateau after 60 cycles. For the control tube (green line) with all other components as the sample tube except the template DNA, there was no increase of fluorescence throughout the same PCR cycles.

Real time PCR products were verified by agarose gel electrophoresis. A DNA fragment of size between 200-250 bp in reference of DNA size standards (100 bp ladder, Biolabs, MA) was obtained for the sample tube. There was no DNA fragment for the control tube (FIG. 9).

Example 2

5'→3' Exonuclease Activity in Taq Polymerase Releases Fluorescence

A set of q-primer and reverse primer (Table 2) was designed to amplify 18s rDNA in soybean genomic DNA. Soybean genomic DNAs were extracted from soybean using DNeasy® plant mini kit (Qiagen). Taq polymerase (Roche) and Vent (exo-) Polymerase without 5'>3' exonuclease activity (New England Biolabs) were used in PCR reactions. Real-time PCR reactions were carried out on a LightCycler® (Roche Molecular Biochemicals) with a 25 μl final volume. Each reaction contained 400 μM dNTPs, 0.2 μM Q-primer and 0.4 μM reverse primer, 2.5 U Taq polymerase (Roche) and 1×Taq polymerase buffer or Vent® (exo-) and 1× buffer (New England Biolabs), 3.0 mM $MgCl_2$ and template DNA. Reaction conditions were an initial denaturation at 95° C. for 2 min, followed by 70 cycles of 95° C. for 15 sec, 55° C. annealing for 15 sec and 72° C. extension for 25 sec, a single fluorescence measurement was made on channel 1 (Ex/Em=470/530 nm) for each cycle at extension step and data processed by LightCycler Software (version 3, Roche) and cycle threshold (Ct) value calculated. PCR products were also analyzed on 2.0% agarose gel.

TABLE 2

Details of Primers and Artificial Templates

| Target gene | Primer ID | Orientation | Sequence (SEQ ID NO:) | Amplicon |
|---|---|---|---|---|
| Soybean 18s rDNA | Q-primer | 1sense | BODIPY ® FL-5'CCTCGTCGCCGCCTGTTCCTAATA CAATAGGAACAGGCGGCGACGAGGGA*TGGGG AATCTTGGACAATGG*3' (4) | 219 bp |
| | 18s-r1 | antisense | 5'CCGATTCACCGCCTACGT3' (5) | |
| Cry1A(C) | Q-primer | 2sense | BODIPY FL-5'CCTCGTCGCCATACAAGGCGACG AGGG*GAGCGTGTCTGGGGTCCTGATTC*3' (6) | 128 bp |
| | Bt-rp1 | antisense | 5'CGGATAGGGTAGGTTCTGGAGTCA3' (7) | |
| RRS3'junction | 060320-P1 | sense | BODIPY FL-5'CCTCGTCGCCATACAAGGCGACG AGGG*TAGCATCTACATATAGCTTC*3' (8) | 85 bp |
| | 060310-2 | antisense | 5'GACCAGGCCATTCGCCTCA3' (9) | |
| Cry1A(c) | TAMRA-P | sense | TAMRA-5'CCTCGTCGCCATACAAGGCGACGAG GGGAGCGTGTCTGGGGTCCTGATTC3' (10) | 47 bp |
| | 060314-1 | antisense | 5'GAGCGGCGTTTCCCATAGTTCC3' (11) | |
| Artificial cry1A(c) part | 060314-13 | template | 5'TGAGCGTGTCTGGGGTCCTGATTCAGGAACT ATGGGAAACGCCGCTCT3' (12) | 48 bp |
| Artificial RRS3'junction | 060425-1 | template | 5'ATAGCATCTACATATAGCTTCTCGTTGTTAGA AAAACAAAACTATTTGGGATCGGAGAAGAACT GTTTGAGGCGAATGGCCTGGTCG3' (13) | 85 bp |

HPTLC plate silica gel 60 F254 20 by 10 cm from Merck (Germany) was used as the stationary phase. 50 μl of real time PCR products were collected by centrifugation and concentrated to 10 μl with Centricon (Eppendorf). 3 μl was sprayed on the silica gel plate as 6 mm bands (2 mm apart) by nitrogen gas with a Linomat 5 (CAMAG), 15 mm from lower edge of the plate, marked with a 6 nt oligo labeled with BODIPY® FL at 5' end (Sigma-Proligo). Development was conducted in a 20 by 10 cm CAMAG twin trough chamber, saturated for 20 min, with 10 ml of freshly prepared developing solvent (ammonium hydroxide:1-propanol=7:11) per trough at a developing distance of 90 mm from the lower edge of the plate. The plate was dried in a fume hood, then photographed under UV light (366 nm) in a CAMAG Reprostar 3 chamber.

During the progression of PCR, fluorescence was only present for the reaction with Taq polymerase but not the one with Vent (exo-) polymerase (FIG. 10A). However, agarose gel electrophoresis of PCR products detected the expected 219 bp PCR products for both reactions (FIG. 10B). This result suggests that while both polymerases could generate PCR products, the fluorescence generated was linked to the presence of 5'-3' exonuclease activity in Taq polymerase. The PCR products were further analyzed by HPTLC. The major band was at the same size as free BODIPY® FL (FIG. 10C) from PCR reaction in the presence of Taq polymerase. It further proves that deletion by 5'>3' exonuclease activity releases BODIPY® FL fluorescence.

Example 3

Detection of Bt Gene in GM Rice and Cotton

PCR primer pair Q-primer 2/bt-rp1 (Table 2) was used in a real time PCR to detect the presence of a 128 bp conserved region of Cry1A(C) gene in transgenic rice and transgenic cotton. All genomic DNAs were extracted from rice and cotton leaf samples using DNeasy® plant mini kit (Qiagen) with quantity and quality verified with agarose gel electrophoresis. Real-time PCR reactions were carried out on a LightCycler® (Roche Molecular Biochemicals) with a 25 µl final volume. Each reaction contained 400 µM dNTPs, 0.2 µM Q-primer and 0.4 µM reverse primer, 2.5 U Taq polymerase (Roche) and 1×Taq polymerase, 3.0 mM $MgCl_2$ and template DNA. Reaction conditions were an initial denaturation at 95° C. for 2 min, followed by 70 cycles of 95° C. for 15 sec, 55° C. annealing for 15 sec and 72° C. extension for 25 sec, a single fluorescence measurement was made on channel 1 (Ex/Em=470/530 nm) for each cycle at extension step and data processed by LightCycler Software (version 3, Roche) and cycle threshold (Ct) value calculated. PCR products were also analyzed on 2.0% agarose gel.

Q-priming PCR was used to detect a 128 bp Bt conserved region in Bt-rice genomic DNA 5 fold serial diluted to DNA quantity ranging from 5 ng to 0.01 ng, also to Bt rice DNA mixed with non GM rice DNA to 5%, 2%, 1% and 0.5% of total DNA. Average values of three replicates are given in Table 3. The absolute limit of detection in rice reached 0.01 ng, equivalent to 20 copies, as low as 0.5% of transgenic DNA mixed with DNA from the wild type could be detected with confidence (Table 3).

TABLE 3

Detection Limit of Q-priming System for Bt Rice.

| | Bt rice DNA | | | | | | | | |
|---|---|---|---|---|---|---|---|---|---|
| | 5 ng | 1 ng | 0.2 ng | 0.04 ng | 0.01 ng | 5% | 2% | 1% | 0.5% |
| Ct value | 34.9 | 39.2 | 45.5 | 49.4 | 57.0 | 26.3 | 28.3 | 30.8 | 36.3 |

Q-priming PCR was used to detect Bt-cotton genomic DNAs serial diluted to 10 ng, 2 ng, 0.4 ng and 0.1 ng. Results for three replicates are given in Table 4. For transgenic cotton, the absolute limit of detection reached 0.1 ng, equivalent to 32 copies (Table 4).

TABLE 4

Detection Limit of Q-priming System for Bt Cotton.

| Bt cotton DNA | 10 ng | 2 ng | 0.4 ng | 0.1 ng |
|---|---|---|---|---|
| Ct value | 28.5 | 31.8 | 34.6 | 41.4 |

Example 4

Mutagenesis Detection Using Q-Priming System

To investigate sensitivity of q-priming system to mutations at target DNA regions, we evaluated impact of mutations at different positions of a reverse primer on Ct of amplification (FIG. 11). Two 48 nt templates (Table 5) were synthesized with some variable sequences at priming site for reverse primers. Different reverse primers were designed to have mutations to various parts of template 1 and 2 (FIG. 11A). PCR reactions were conducted with Taq polymerase by Q-primer 2 (Table 2) with each of the reverse primers. Real-time PCR reactions were carried out on a LightCycler® (Roche Molecular Biochemicals) with a 25 µl final volume. Each reaction contained 400 µM dNTPs, 0.2 µM Q-primer and 0.4 µM reverse primer, 2.5 U Taq polymerase (Roche) and 1×Taq polymerase, 3.0 mM $MgCl_2$ and template DNA. Reaction conditions were an initial denaturation at 95° C. for 2 min, followed by 60 cycles of 95° C. for 15 sec, 55° C. annealing for 15 sec and 72° C. extension for 25 sec, a single fluorescence measurement was made on channel 1 (Ex/Em=470/530 nm) for each cycle at extension step and data processed by LightCycler Software (version 3, Roche) and cycle threshold (Ct) value calculated. Fluorescence was monitored during progress on PCR.

TABLE 5

Primers and Artificial Templates

| Target | Name (ID in FIG. 11B) | Sequence (5'-3') (SEQ ID NO:) |
|---|---|---|
| | Artificial template 1 | tgagcgtgtctggggtcctgattcagg aactatgggaaacgccgctct (14) |
| | Artificial template 2 | tgagcgtgtctggggtcctgattcaaa ggctaggtgaaccgcagcctt (15) |
| Template 1 | mt-rp 1 (10) | gagcggcgtttcccatagttcc (16) |
| Template 1 | mt-rp 2 (15) | gagcggcgtttctaatagttcc (17) |
| Template 1 | mt-rp 3 (14) | gagcggcgtttcccatagttat (18) |
| Template 1 | mt-rp 4 (13) | gagcggcgtttctcatagttcc (19) |
| Template 1 | mt-rp 5 (12) | gagcggcgtttcccatagttac (20) |

TABLE 5-continued

Primers and Artificial Templates

| Target | Name (ID in FIG. 11B) | Sequence (5'-3') | (SEQ ID NO:) |
|---|---|---|---|
| Template 1 | mt-rp 6 (11) | gagcggcgtttcccatagttct | (21) |
| Template 2 | mt-rp 7 (20) | aggctgcggttcacctagcctt | (22) |
| Template 2 | mt-rp 8 (25) | aggctgcggcgcacctagcctt | (23) |
| Template 2 | mt-rp 9 (24) | aggctgcggttcacctagccgc | (24) |
| Template 2 | mt-rp 10 (23) | aggctgcggtgcacctagcctt | (25) |
| Template 2 | mt-rp 11 (22) | aggctgcggttcacctagccct | (26) |
| Template 2 | mt-rp 12 (21) | aggctgcggttcacctagcctc | (27) |

It was found out that mutation to 3' end of the primers affected Ct value most while mutations to other parts of the primer had little impact on Ct value. One single nucleotide mutation from C>T at 3' end had Ct value 10.9 more than that of PCR with wild-type primer. Mutations to the two continuous C nucleotides to TA at 3' ends increased the Ct value 33.6 higher. Similar level increases of Ct value were also obtained in the case of T to C and TT to CG for template 2 (FIGS. 11B and 11C).

Example 5

Dual Color Detection Using Q-Priming System

BODIPY® FL labeled Q-primer 060320-P1 and reverse primer 060310-2 amplify artificial template 060425-1 (Table 2). TAMRA labeled Q-primer TAMRA-P and reverse primer 060314-1 amplify artificial template 060314-13 (Table 2). Real-time PCR reactions were carried out on a LightCycler® (Roche Molecular Biochemicals) with a 25 μl final volume. Each reaction contained 400 μM dNTPs, 0.2 μM each Q-primer and 0.4 μM each reverse primer, $10^{12}$ copies each template, 2.5 U Taq polymerase (Roche) and 1×Taq polymerase, 3.0 mM $MgCl_2$ and template DNA. Reaction conditions were an initial denaturation at 95° C. for 2 min, followed by 50 cycles of 95° C. for 15 sec, 55° C. annealing for 15 sec and 72° C. extension for 25 sec, a single fluorescence measurement was made on channel 1 (530 μm) and channel 2 (640 nm) for each cycle at extension step and data processed by LightCycler Software (version 3, Roche) and cycle threshold (Ct) value calculated. Fluorescence was monitored during progress on PCR. We observed increase of fluorescent intensity from TAMRA labeled q-priming PCR on channel 2, but no increased fluorescent intensity from BODIPY® FL labeled q-priming PCR (FIG. 12A). However, on channel 1, increased fluorescent intensity can be observed from BODIPY FL labeled q-priming PCR, but no increased fluorescent intensity from TAMRA labeled q-priming PCR (FIG. 12B). This illustrate that (1) multiplex PCR with BODIPY® and TAMRA labeled primers shows no interference to each other and (2) two different targets can be amplified simultaneously.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Beaucage and Caruthers (1981). Studies on nucleotide chemistry v. deoxynucleoside phosphoramidites: a new class of key intermediates for deoxypolynucleotide synthesis. *Tetrahedron Letts* 22:1859-1862.

Bustin, S. A. (2000). Absolute quantification of mRNA using real-time reverse transcription polymerase chain reaction assays. *J Molecular Endocrinology* 25:169-193.

Clegg, R. M. (1992). Fluorescent resonance energy transfer and nucleic acids. *Methods Enzymol* 211:353-388.

Edwards, M. C. and Gibbs, R. A. (1994). "Multiplex PCR: Advantages, Development, and Applications," *PCR Methods and Applications* 3:S65-S75.

Henegariu, O. et al. (1997). "Multiplex PCR: Critical parameters and Step-by-step protocol." *Biotechniques* 23:504-511.

Horn, T. et al. (1997). Chemical synthesis and characterization of branched oligodeoxyribo-nucleotides (bDNA) for use as signal amplifiers in nucleic acid quantification assays. *Nucleic Acids Res* 25:4842-4849.

Kaboev, O. K. et al. (2000). PCR hot start using primers with the structure of molecular beacons (hairpin-like structure). *Nucleic Acids Res* 28:e94

Kurata, S. et al. (2001). Fluorescent quenching-based quantitative detection of specific DNA/RNA using a BODIPY® FL-labeled probe or primer. *Nucleic Acids Res* 29(6):e34.

Livak, K. J. et al. (1995). Oligonucleotides with fluorescent dyes at opposite ends provide a quenched probe system useful for detecting PCR product and nucleic acid hybridization. *PCR Methods Appl* 4:357-62.

Mackay, I. M. et al. (2002). Real-time PCR in virology. *Nucleic Acids Res* 30:1292-1305.

Myakishev, M. V. et al. (2001). "High-throughput SNP genotyping by allele-specific PCR with universal energy-transfer-labeled primers." *Genome Res* 11:163-9.

Nazarenko, I. A. et al. (1997). A closed tube format for amplification and detection of DNA based on energy transfer. *Nucleic Acids Res* 25:2516-2521.

Needham-VanDevanter, D. R. et al. (1984). Characterization of an adduct between CC-1065 and a defined oligodeoxynucleotide duplex. *Nucleic Acids Res* 12:6159-6168.

Nelson, P. S. et al. (1989). Bifunctional oligonucleotide probes synthesized using a novel CPG support are able to detect single base pair mutations. *Nucleic Acids Res* 17:7187-7194.

Nielsen, P. E. et al. (1991). Sequence-selective recognition of DNA by strand displacement with a thymine-substituted polyamide. *Science* 254:1497-1500.

Poddar, S. K. (2000). Symmetric vs. asymmetric PCR and molecular beacon probe in the detection of a target gene of adenovirus. *Molecular and Cellular Probes* 14:25-32.

Proudnikov, D. and Mirzabekov, A. (1996). Chemical methods of DNA and RNA fluorescent labeling. *Nucleic Acids Res* 24:4535-4542.

Rhodes, C. H. et al. (1997). "Analysis of the allele-specific PCR method for the detection of neoplastic disease." *Diagn Mol Pathol* 6:49-57.

Schmalzing, D. et al., (1999). "Two-color Multiplexed Analysis of Eight Short Tandem Repeat Loci with an Electrophoretic Microdevice," *Anal Biochem* 270:148-152.

Schofield, P. et al. (1997). Molecular beacons: trial of a fluorescence-based solution hybridization technique for ecological studies with ruminal bacteria. *Applied and Environmental Microbiology* 63:1143-1147.

Shaw, B. R. et al. (1993). Oligonucleoside boranophosphate (borane phosphonate) oligomers. *Methods Mol Biol* 20:225-243.

Shaw, B. R. et al. (2000). Boranophosphate backbone: a mimic of phosphodiesters, phosphorothioates, and methylphosphonates. *Methods Enzymol* 313:226-257.

Tani, H., et al. (2005). Quantification of genetically modified soybean by quenching probe (qprobe)-pcr. *J Agric Food Chem* 53:2535-2540.

Tyagi, S. and Kramer, F. R. (1996). Molecular beacons: probes that fluoresce upon hybridization. *Nature Biotechnology* 14:303-308.

Zhang, Y. et al. (2003). A novel real-time quantitative PCR method using attached universal template probe. *Nucleic Acids Res* 31(20):e123.

What is claimed is:

1. A self-quenching primer consisting of the structure Q-5'-$C_n$—X-$G_{(n+1)}$-$Y_m$—Z-3', wherein n is 0-10, m is 0 or 1, X is an oligonucleotide sequence that forms a hairpin, Y is a nucleotide linker sequence, Z is an oligonucleotide that is target specific sequence and Q is a fluorophore that is quenched by guanine and wherein the hairpin has a Tm of 80° C. to 90° C.

2. The self-quenching primer of claim 1, wherein Q is BODIPY® FL, another variant of BODIPY®, TAMRA or a fluorescein.

3. The self-quenching primer of claim 1, wherein Y comprises 1-5 nucleotides.

4. The self-quenching primer of claim 1, wherein Z comprises 5-40 nucleotides.

5. The self-quenching primer of claim 4, wherein Z comprises 15-30 nucleotides.

6. The self-quenching primer of claim 1, wherein the 5' arm and the 3' arm of the hairpin are each 5-11 nucleotides in length.

7. The self-quenching primer of claim 1, wherein n is 0-5.

8. A method for amplifying a target nucleotide sequence or reverse complement thereof, the method comprising:
   providing a template nucleic acid comprising a first strand, the first strand comprising a target region that comprises a target nucleotide sequence or its reverse complement;
   providing a self-quenching primer consisting of a region of identity to a 5' subregion of the target region, wherein the self-quenching primer comprises the structure Q-5'-$C_n$—X-$G_{(n+1)}$-$Y_m$—Z-3', wherein n is 0-10, m is 0 or 1, X is an oligonucleotide sequence that forms a hairpin, Y is a nucleotide linker sequence, Z is an oligonucleotide that is a target specific sequence and Q is a fluorophore that is quenched by guanine and wherein the hairpin has a Tm of 80° C. to 90° C.;
   providing a linear primer comprising a region of complementarity to a 3' subregion of the target region;
   contacting the template nucleic acid, the self-quenching primer and the linear primer; and extending the self-quenching and linear primers, thereby amplifying at least a portion of the target nucleotide sequence or its reverse complement.

9. The method of claim 8, wherein the 3' nucleotide of the self-quenching primer or the linear primer is complementary to a wild type allele or a mutant allele.

10. The method of claim 8, which further comprises simultaneously amplifying a second target nucleotide sequence or reverse complement thereof by providing a second template nucleic acid comprising a second target region, a second self-quenching primer comprising a region of identity to a 5' subregion of the second target region and a second linear primer comprising a region of complementarity to a 3' subregion of the second target region.

11. The method of claim 8, wherein the fluorophore is BODIPY® FL, another variant of BODIPY®, TAMRA or a fluorescein.

12. The method of claim 10, wherein the each self-quenching primer comprises a different fluorophore and the fluorophore is BODIPY® FL, another variant of BODIPY®, TAMRA or a fluorescein.

13. The method of claim 8, wherein the fluorophore is released by 5'-3' nuclease activity during extension of the linear primer.

14. The method of claim 8 which further comprises detecting the emitted fluorescence.

15. The method of claim 14, wherein the emitted fluorescence is measured in real time.

16. The method of claim 14 which further comprises determining the amount of template nucleic acid initially present.

17. The method of claim 8, wherein the template nucleic acid is selected from the group consisting of a single-stranded DNA product of a reverse transcription reaction, a double-stranded cDNA, a single-stranded PCR product, a double-stranded PCR product and a genomic DNA.

18. The method of claim 8, wherein the amplification detects the presence or absence of the target nucleotide sequence in a sample.

19. The method of claim 18, wherein the sample is a forensic sample.

20. The method of claim 18, wherein the sample is diagnostic sample.

21. The method of claim 18, wherein the sample is suspected of containing a genetically modified organism or a transgene thereof.

22. The method of claim 21, wherein the sample is a sample of an organism or part thereof.

23. The method of claim 21, wherein the sample is a mixture of organisms or parts thereof.

24. The method of claim 22, wherein the organism is a plant or a plant part.

25. The method of claim 21, wherein the sample is processed food.

26. A composition comprising:
a template nucleic acid comprising a first strand, the first strand comprising a target region that comprises a target nucleotide sequence or its reverse complement;
a self-quenching primer consisting of a region of identity to a 5' subregion of the target region, wherein the self-quenching primer comprises the structure Q-5'-$C_n$—X-$G_{(n+1)}$-$Y_m$—Z-3', wherein n is 0-10, m is 0 or 1, X is an oligonucleotide sequence that forms a hairpin, Y is a nucleotide linker sequence, Z is an oligonucleotide that is target specific sequence and Q is a fluorophore that is quenched by guanine and wherein the hairpin has a Tm of 80° C. to 90° C.; and
a linear primer comprising a region of complementarity to a 3' subregion of the target region.

27. The composition of claim 26, wherein the fluorophore is BODIPY® FL, another variant of BODIPY®, TAMRA or a fluorescein.

28. The composition of claim 26 further comprising a polymerase.

29. The composition of claim 28, wherein the polymerase has 5'-3' nuclease activity.

30. The composition of claim 26, wherein the template nucleic acid is selected from the group consisting of a single-stranded DNA product of a reverse transcription reaction, a double-stranded cDNA, a single-stranded PCR product, a double-stranded PCR product and a genomic DNA.

31. The composition of claim 26, wherein the composition is contained in a thermal cycler.

32. A kit for use in amplifying a target nucleotide sequence or reverse complement thereof from a template nucleic acid strand comprising a target region that comprises the target nucleotide sequence or its reverse complement, the kit comprising:
a self-quenching primer consisting of a region of identity to a 5' subregion of the target region, wherein the self-quenching primer comprises the structure Q-5'-$C_n$—X-$G_{(n+1)}$-$Y_m$—Z-3', wherein n is 0-10, m is 0 or 1, X is an oligonucleotide sequence that forms a hairpin, Y is a nucleotide linker sequence, Z is an oligonucleotide that is target specific sequence and Q is a fluorophore that is quenched by guanine and wherein the hairpin has a Tm of 80° C. to 90° C.; and
a linear primer comprising a region of complementarity to a 3' subregion of the target region packaged in one or more containers.

33. The kit of claim 32, wherein the fluorophore is BODIPY® FL, another variant of BODIPY®, TAMRA or a fluorescein.

34. The kit of claim 32 further comprising one or more of: a polymerase, a buffer, a standard template for calibrating a detection reaction, instructions for extending the hairpin primer to amplify at least a portion of the target nucleotide sequence or reverse complement thereof, instructions for using the components to amplify, detect and/or quantitate the target nucleotide sequence or reverse complement thereof, or packaging materials.

* * * * *